Nov. 1, 1938. C. H. LOTHROP Plant Pat. 302
SNAPDRAGON
Filed July 31, 1937
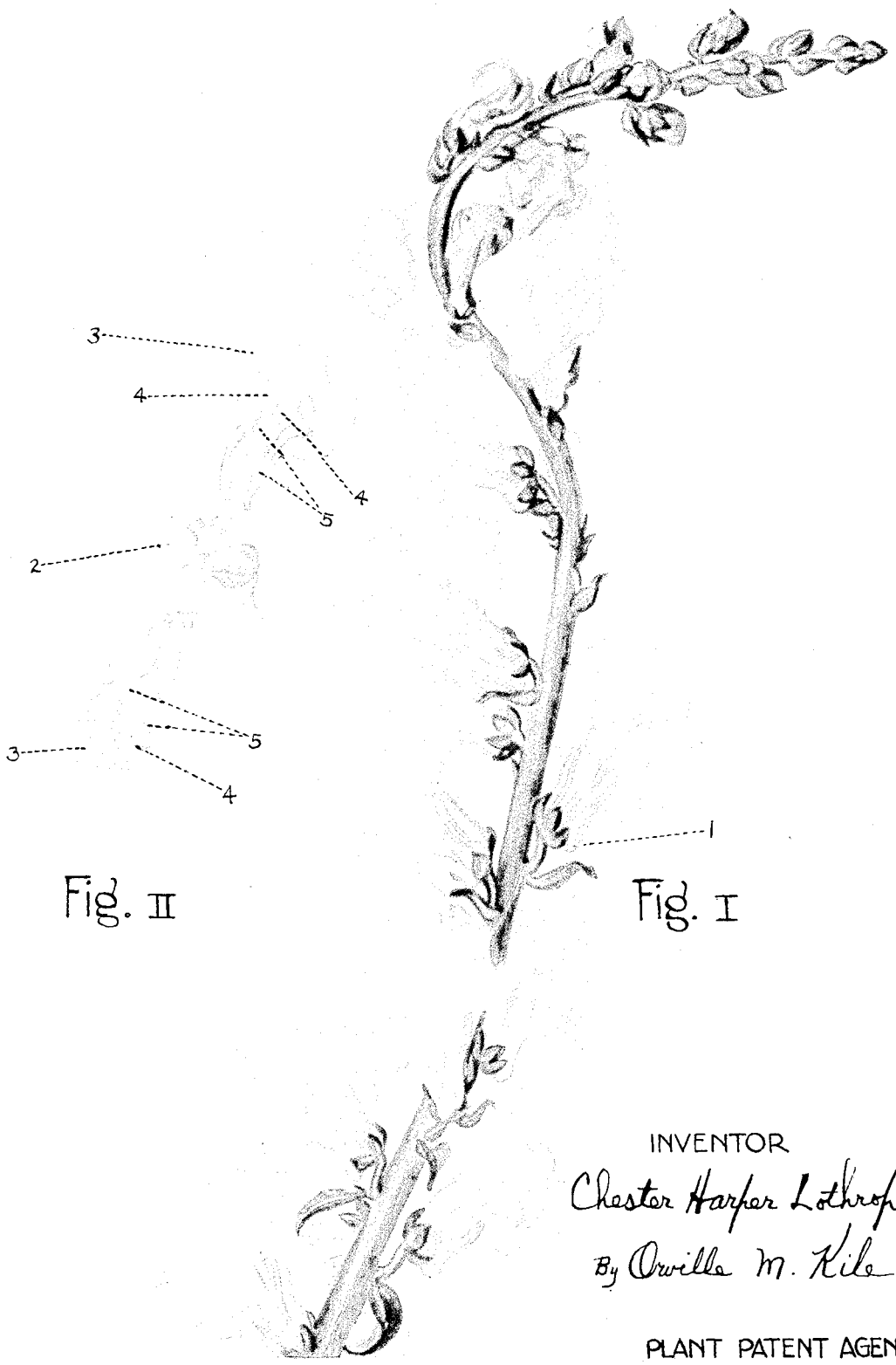
Fig. II
Fig. I
INVENTOR
Chester Harper Lothrop
By Orville M. Kile
PLANT PATENT AGENT Patented Nov. 1, 1938

Plant Pat. 302

UNITED STATES PATENT OFFICE

302

SNAPDRAGON

Chester Harper Lothrop, Lexington, Mass.

Application July 31, 1937, Serial No. 156,815

1 Claim. (Cl. 47—60)

The present variety was developed as a seedling in the course of selection of the best varieties from year to year in an effort to improve pink snapdragons. A pink sport of Lucky Strike (a white snapdragon) showed promising characteristics and cuttings were rooted, potted, brought into blossom and placed in a house of potted seedlings of the varieties Cheviot Maid and Winter Helen. The following year the seeds which I had saved from these cuttings were planted and there resulted strong plants with blossoms of a great variety of colors, the crossing doubtless having been done by bees and the pollen parent having been probably one of the two varieties mentioned. In collecting the seeds from this planting, probably some were dropped or a few pods left on the plants and these soon came up as seedlings in the ashes on the greenhouse bench. The present variety was one of these latter seedlings. It was very noticeable and seemed different from the rest so I carefully nurtured it until it bloomed and I found that I had an entirely new kind of snapdragon.

I have asexually reproduced the new variety by cuttings through three generations and the characteristics have persisted.

The principal characteristics of this variety are its one hundred percent doubleness, its large size, the tenacity of its flower, its long-lasting quality, and its distinctive color as applied to double snapdragons. Another feature which makes this variety desirable is the fact that the bees do not work on it in the Spring therefore no harm from that source is done the spikes when at their best.

The accompanying illustration shows in full color and approximately natural size in the original, a portion of one of the spikes since there was not room for the entire spike (as Fig. I), and an individual flower which has been spread open to show the inner petals and the multiple growth of the center (as Fig. II).

This variety grows as high as any commercial variety and has been known to have as many as sixty blossoms and buds on a single stalk at one time, of which about two-thirds would be fully opened blossoms. Flower spikes are sometimes 2 feet long and 4 or 5 inches in diameter.

The flower spike is exceedingly long-lasting, due to the combination of the habit of the lower flowers of clinging tenaciously and of the buds at the top of the spike of continuing progressively to open.

Greatly increasing the double effect of the lower blossoms on the spike is the unusual and remarkable development of additional blossoms within each of these lower blossoms. In other words, at the center of the blossom there is a rudimentary spike (2 in Fig. II) which develops as the flower grows older, sometimes developing as many as three or four buds to the color stage before the original blossom dries up. Each of these additional blossoms has the same unusual central construction as is found in the original and sometimes these continue to open progressively one from the inside of the other.

Following is a more detailed description of the flower and plant.

*The plant*

Growth habit:

Very strong and vigorous.

Blooming habit:

This new variety is a continuous bloomer. Its largest burst of bloom appears in February in my greenhouses, where I have planted in August or September, but there is continuous bloom throughout the winter and spring. It will also bloom in pots in summer. A strong second growth occurs on this variety.

Foliage:

Rich and abundant.

*Leaves.*—Cedar green (Plate VI of Ridgway's Color Standards and Nomenclature) on upper side. Light Helibore Green (Plate XVII) on under side.

Stems:

Stiff and erect. Very strong. Courge Green (Plate XVII).

Flower spikes:

Often attain a length of 2 feet and a diameter of 4 to 5 inches. The end of the spike containing buds is gracefully curved and drooping rather than stiff.

Arrangement of flowers on stem:

Flowers appear irregularly around the stem at frequent but irregular intervals.

*The flower*

Blossom:

*Color.*—Color deepens as spring advances. The general color effect at a glance in late spring is Rose Pink (Plate XII) but upon closer examination of the individual petals several shades of pink are noted, ranging from Rose Pink (Plate XII) through Thulite Pink (Plate XXVI), to a slight amount of Deep Rose Pink (Plate XII). Some of the smaller petals have small spots of yellow at the point where they attach or turn backward. The inside of the flower tube shows considerable white.

*Size, shape, and appearance.*—The corolla of the blossom consists of a tube about three-fourths of an inch long which divides into two large lips, the upper one consisting of two petals and the under one consisting of three petals (3 in Fig. II) as in the usual single varieties. In addition to these petals there are attached to the inside of these petals several smaller petal-like growths (4 in Fig. II) which are the expansion and elaboration of the reproductive organs. Usually there are five of these petal-like structures attached to the inside of the upper lip. White ridges (5 in Fig. II) extend upward to the point at which the tube separates. On the lower lip these ridges are flanked by yellow hair-like appendages. At the point at which the tube separates, these ridges enlarge into ruffled petals which protrude from the corolla tube (4 in Fig. II). At the base of the blossom the lower part of the corolla protrudes into a sort of pocket (1 in Fig. I). The average length of blossom is 1½ to 2 inches. The occurrence of rudimentary spikes and buds within the blossom has been described above.

Peduncle:

Short, strong.

Sepals:

Five, short, Courge Green (Plate XVII).

Having thus disclosed my invention, I claim:

A new variety of snapdragon substantially as herein shown and described, characterized particularly by its vigorous growth of large, strong spikes, beset with unusually large numbers of buds and blossoms, the latter being extremely double, large in size, very tenacious thus giving long-lasting quality, and having a distinctive Rose Pink to Deep Rose Pink color as applied to double snapdragons.

CHESTER HARPER LOTHROP.